(12) United States Patent
Otsubo (10) Patent No.: US 7,582,077 B2
(45) Date of Patent: Sep. 1, 2009

(54) WEARING ARTICLE

(75) Inventor: Toshifumi Otsubo, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 160 days.

(21) Appl. No.: 11/092,701

(22) Filed: Mar. 30, 2005

(65) Prior Publication Data

US 2005/0222552 A1    Oct. 6, 2005

(30) Foreign Application Priority Data

Mar. 31, 2004  (JP) .............................. 2004-108176
Nov. 9, 2004   (JP) .............................. 2004-325646

(51) Int. Cl.
*A61F 13/15*   (2006.01)
*A61F 13/20*   (2006.01)
*A41B 9/00*    (2006.01)
*A44B 18/00*   (2006.01)
*B01D 33/00*   (2006.01)
*B65H 21/00*   (2006.01)

(52) U.S. Cl. .......................... 604/391; 604/386; 2/78.4; 24/31 V (58) Field of Classification Search .......... 604/386–399
See application file for complete search history.

(56) References Cited

U.S. PATENT DOCUMENTS 4,701,179 A * 10/1987 Kellenberger et al. ....... 604/394
5,009,653 A *  4/1991 Osborn, III ............ 604/385.04
6,102,901 A *  8/2000 Lord et al. .................. 604/386
6,715,188 B1* 4/2004 Jackson et al. ............. 24/698.1
6,752,796 B2* 6/2004 Karami ....................... 604/391
2002/0032428 A1* 3/2002 Lindstrom et al. .......... 604/392
2002/0038110 A1* 3/2002 Kusibojoska et al. ....... 604/392
2003/0126724 A1* 7/2003 Kono et al. .................... 24/451

FOREIGN PATENT DOCUMENTS

JP       1983-203101        11/1983
JP       1995-90032         10/1995
WO       02/26183            4/2002

OTHER PUBLICATIONS

Taber Industries, "Stiffness Tester-Interpreting Results", http://www.taberindustries.com/Products/stiffness_tester/Taber_Stiffness_Tester_Interpreting_Results.asp?ct=1&sc=5.*
Patent Abstracts of Japan—Publication No. 09-075393, Published Mar. 25, 1997.
Patent Abstracts of Japan—Publication No. 2002-045214, Published Feb. 12, 2002.

* cited by examiner

*Primary Examiner*—Melanie J Hand
(74) *Attorney, Agent, or Firm*—Lowe Hauptman Ham & Berner

(57) ABSTRACT

A wearing article includes a chassis having front and rear waist regions, a fastener mechanism adapted to fasten transversely opposite side edges of the chassis, and an elastic adjusting element adapted to stretch or contract at least one of the front and rear waist regions in a transverse direction. The fastener mechanism includes flat and rigid male fastener panels each having a proximal end secured to the side edge of the rear waist region, and female fastener members located on the side edges of the front waist region so that the male fastener panels can be releasably engaged with the respective female fastener members.

8 Claims, 9 Drawing Sheets

WEARING ARTICLE

RELATED APPLICATIONS

The present application is based on, and claims priority from, Japanese Application Number 2004-108176, filed Mar. 31, 2004 and Japanese Application Number 2004-325646, filed Nov. 9, 2004, the disclosures of which are hereby incorporated by reference herein in their entirety.

BACKGROUND OF THE INVENTION

The present invention relates to wearing articles for receiving bodily discharges in a direct or indirect manner. More particularly, the present invention relates to disposable diapers, diaper covers, training pants, incontinence pants or the like provided with a fixed point type fastener mechanism adapted to hold such an article about an appropriate region of the wearer's body.

It is well known to provide on respective outer surfaces of rear and front waist regions of an article in the vicinity of transversely opposite side edges of the respective waist regions with a pair of fasteners and a pair of target tape strips, respectively, so that the fasteners may be releasably engaged with the target tape strips to connect the front and rear waist regions with each other along the side edges of these waist regions (See Japanese Unexamined Patent Application Publication No. 1983-203101, hereinafter referred to as "Citation 1").

It is also well known to adopt a pair of fixed point type fastener mechanisms as a means to connect front and rear waist regions of an article along the side edges of these waist regions (See Japanese Patent Publication No. 1995-90032, hereinafter referred to as "Citation 2"). The fastener mechanism disclosed in Citation 2 comprises generally V-shaped rigid members located on both side edges of the rear waist region and generally V-shaped rigid members located on both side edges of the front waist region so that those on the rear waist region may be releasably engaged with those on the front waist region.

For the combination of fasteners and target tape strips disclosed in Citation 1, the positions at which the respective associated fastening components should be engaged one with another must be appropriately selected in the course of fastening operation. Should this positioning operation be inappropriate, it will be impossible to fasten the article at the appropriate position of the wearer's body. Consequentially, the article will slip down, resulting in leakage of bodily discharges from the leg-openings. Furthermore, if an excessive shearing force is exerted on the positions of the respective fastening components engaged with one another during use of the article, these components may be unintentionally disengaged from one another.

The fixed point type fastener mechanism disclosed in Citation 2 is certainly free from the problems encountered by the construction disclosed in Citation 1 because the positions of engagement are predetermined. However, the fastening members adapted to be engaged with each other are folded both in a generally V-shape and inevitably become bulky during use of the article. In addition to such bulkiness, these fastening members locally compress the wearer's skin. The more tightly the article is fastened around the wearer's waist, the more significantly the wearer experiences a feeling of discomfort due to the presence of these fastening members.

SUMMARY OF THE INVENTION

In view of the problems as have been described above, it is an object of the present invention to provide a wearing article adopting a fastener mechanism of fixed point type improved to ensure a fastening effect more reliably in proportion to a shearing force exerted on mutually engaging components and thereby to eliminate an anxiety that the article might slip down from the proper position of the wearer's body at which the article should be held or fall off from the wearer's body.

Specifically, there is provided a wearing article comprising a chassis having a longitudinal axis, a transverse axis orthogonal to the longitudinal axis, an inner surface, an outer surface, first and second waist regions cooperating with each other to define a waist-opening and a crotch region extending between the first and second waist regions and cooperating with these two waist regions to define a pair of leg-openings; a faster mechanism serving to connect the first and second waist regions with each other along transversely opposite side edges thereof one to another; and an elastic adjusting means located in at least one of the first and second waist regions so that the elastic adjusting means stretches or contracts this waist region in a direction along the transverse axis.

The fastener mechanism further comprises a pair of male fastener members in the form of flat and rigid panel each having distal and proximal ends spaced from each other in the direction along the transverse axis wherein the distal end extends toward the longitudinal axis and the proximal end is secured to each of the transversely opposite side edges of the first waist region; and a pair of female fastener members located on the transversely opposite side edges of the second waist region so that the male fastener members are releasably engaged with the female fastener members.

In the wearing article according to the present invention, the fastener mechanism used to connect the waist regions along the side edges of the respective waist regions is of fixed point type. Such a fastener mechanism of fixed point type advantageously eliminates troublesome operation of positioning which otherwise would be required for effective engagement between the male fastener members and the female fastener members. With the article put on the wearer's body, the male fastener members are pressed by the side edges against the wearer's waist as the first and second waist regions are automatically tightened by the elastic adjusting means. The higher a shearing force exerted on the side edges of the first and second waist regions including the male fastener members is, the more tightly the male fastener members are pressed against the wearer's waist. In addition, the male fastener panels have a desired stiffness to serve also as a stabilizing support means for the first and second waist regions. Consequentially, the engagement between the male and female fastener members is reliably held and thereby leakage of bodily discharges due to unintentional slip down of the article. Obviously, there is no possibility that the article might fall away from the wearer's body.

The present invention includes preferred embodiments as follow:

Preferably, the male fastener members have the proximal ends secured to the inner surfaces of the first waist region along the respective side edges and further have finger-grip tabs respectively extending outward from the proximal ends in the direction along the transverse axis beyond the side edges of the first waist region. The presence of such finger-grip tabs allows the first and second waist regions to be orderly connected to each other along the respective side edges and facilitates the male fastener panels to be handled for engagement with and disengagement from the associated female fastener members.

Preferably, the first waist region is provided along side edges thereof with reinforcing zones. According to this embodiment, it is unlikely that the proximal ends of the respective male fastener panels might be detached from the side edges of the waist region and/or damaged even if a relatively high tensile force is exerted on these male fastener panels when the article is put on the wearer's body or during use of the article.

Preferably, the female fastener members are defined by loops created on the outer surface of the second waist region along the side edges thereof or by slits provided in the second waist region along side edges thereof. Such an embodiment facilitates the female fastener members to be formed without using any separate members.

Preferably, the male fastener panels are provided on the distal ends thereof with hooks. This embodiment ensures that the male fastener panels further engage the respective female fastener members.

Preferably, the male fastener panels are made of plastics and adapted to bow in conformity with a contour of the wearer's waist. This embodiment allows the male fastener panels having a desired stiffness to be adopted without an anxiety that the wearer might experience a feeling of discomfort.

Preferably, each of the male fastener panels have a stiffness value in a range of 0.09N/cm to 3N/cm as measured by Taber's method, a dimension in a range of 5 to 50 mm as measured in the direction along the longitudinal axis and a dimension in a range of 20 to 60 mm as measured in the direction along the transverse axis. According to this embodiment, it is unlikely that these male fastener panels might uncomfortably irritate the wearer's skin. In addition, these male fastener panels sufficiently function as the stabilizing support means for the first and second waist regions so that none of gathers is created along the side edges of the first and second waist regions and the vicinity thereof and thereby a good appearance is maintained. According to this embodiment, one of the first and second waist regions may be formed using an elastically stretch- and contractable nonwoven fabric of well known art.

Preferably, the chassis comprises a liquid-pervious inner sheet, a liquid-impervious outer sheet and a liquid-absorbent core interposed between these two sheets. According to this embodiment, one of the first and second waist regions may be formed using an elastically stretch- and contractable nonwoven fabric of well known art.

Preferably, the chassis comprises a liquid-pervious inner sheet, a liquid-impervious outer sheet and a liquid-absorbent core interposed between these two sheets. According to this embodiment, it is easy to provide the absorbent articles such as diapers similar to those of well known art.

DETAILED DESCRIPTION OF THE PREFERRED EMBODIMENTS

Figure 1:
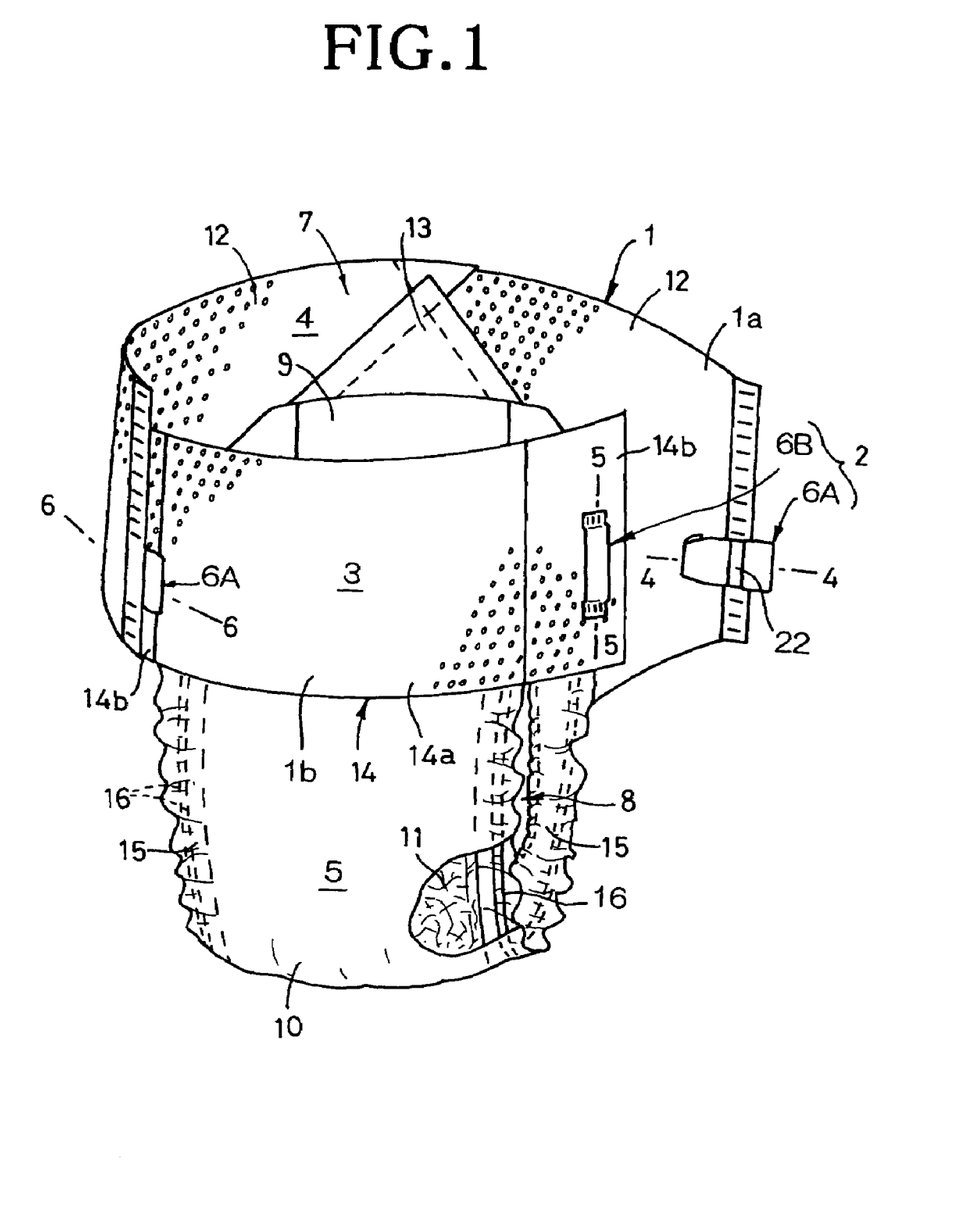
FIG. 1 is a partially cutaway perspective view showing a disposable diaper with first and second waist regions closed along one of both sides of the diaper but opened along the other side.
Figure 2:
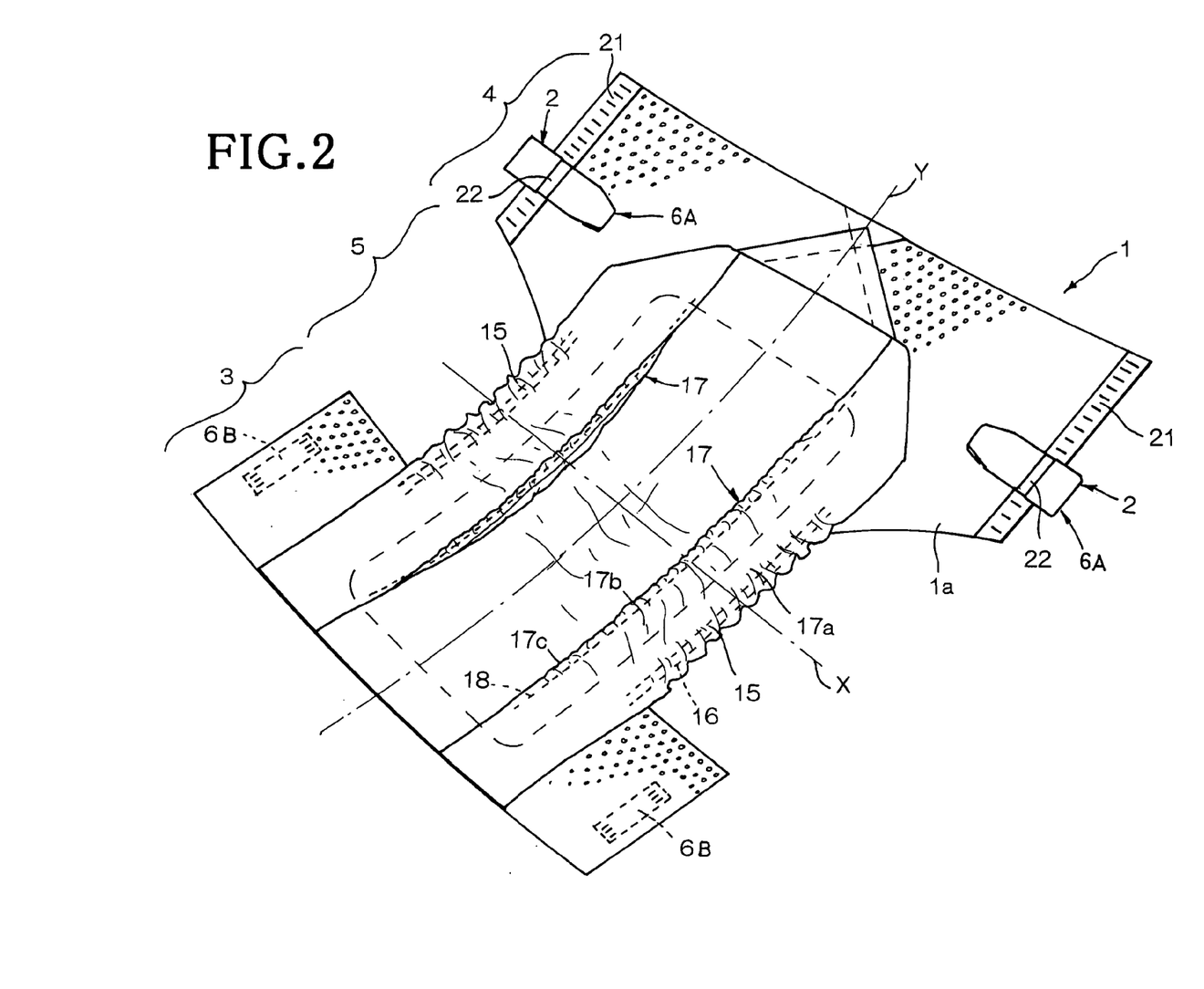
FIG. 2 is a perspective view showing the diaper developed but remaining slightly contracted as opposed to the viewer.
Figure 3:
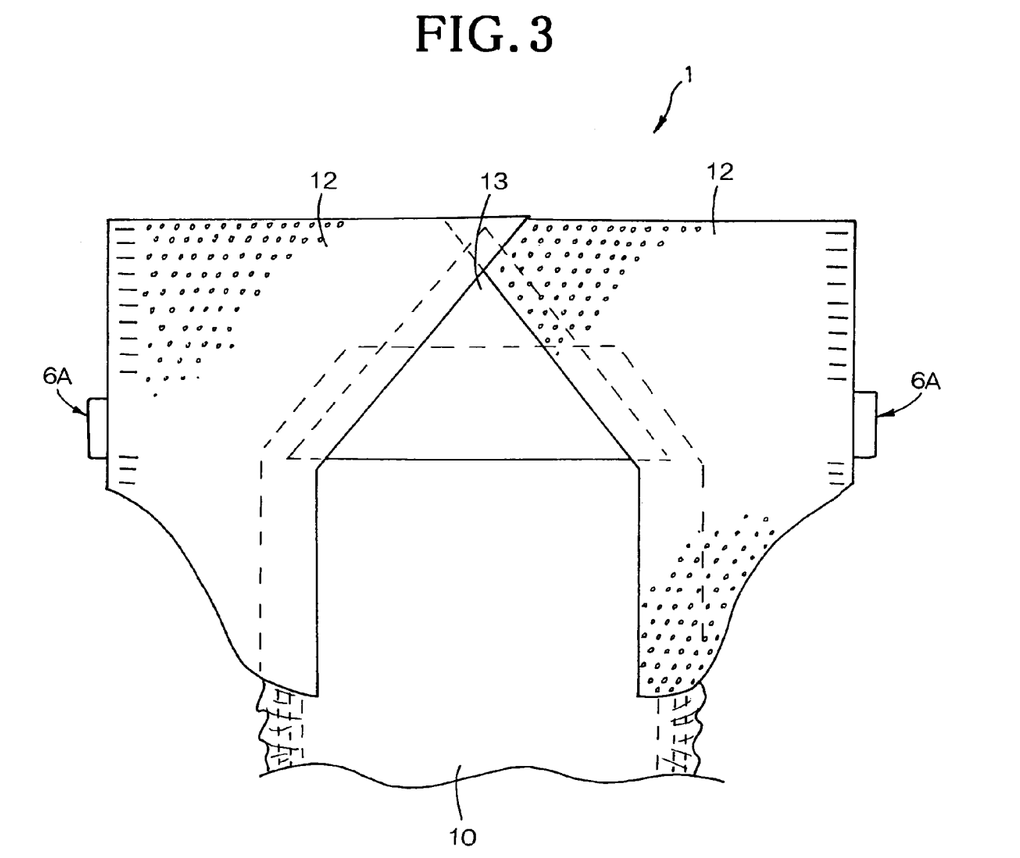
FIG. 3 is a partial plan view showing a rear waist region of the diaper.

FIGS. 1 through 3 show a so-called open-type disposable diaper as a specific embodiment of the present invention. The diaper basically comprises a chassis 1 and a fastener mechanism 2. The chassis 1 has a longitudinal axis Y, a transverse axis X crossing this longitudinal axis X, an inner surface 1a, an outer surface 1b opposed to the inner surface 1a, a front waist region 3, a rear waist region 4 and a crotch region 5 extending between these waist regions 3, 4. The fastener mechanism 2 comprises a pair of flat and rigid male fastener panels 6A located on the inner surface 1a of the rear waist region 4 in the vicinity of respective side edges thereof and a pair of female fastener members located on the outer surface 1b of the front waist region 3 in the vicinity of respective side edges thereof. The male fastener panels 6A are releasably engaged with the female fastener members 6B to assemble the chassis 1 in the pants-type and thereupon to define a waist-opening and a pair of leg-openings 8.

The chassis 1 comprises a liquid-pervious inner sheet 9, a liquid-impervious outer sheet 10 made of a plastic film, and a liquid-absorbent core 11 containing fluff pulp as a base material and immovably interposed between these sheets 9, 10 preferably using hot melt adhesive (not shown) intermittently applied thereto. Depending on a particular intended use of the article, e.g., when the article is a diaper cover, the absorbent core 11 is unnecessary. In other words, construction of the chassis 11 is not limited to the illustrated construction. The chassis 1 further includes, as elastically stretch- and contractable adjusting means, a pair of sheet members 12 made of a nonwoven fabric joined to each other side by side in the rear waist region 4 and having a elastic stretchability with a tensile strength higher than those of the inner and outer sheets 9, 10, a sheet member 13 made of a nonwoven fabric joined to these sheets 12 so as to extend between these sheet members 12, a belt-like member 14 made of a nonwoven fabric joined to the outer surface of the outer sheet 10 in the front waist region 3 and having also a tensile strength higher than those of the inner and outer sheets 9, 10. The belt-like member 14 comprises an elastically stretch- and contractable intermediate segments 14a joined to the outer surface of the front waist region 3 substantially over its middle zone and a pair of end segments 14b respectively joined to longitudinally opposite ends of the intermediate segment 14a and left free from the outer surface of the front waist region 3. Construction of the elastically stretch- and contractable adjusting means is not limited to the illustrated embodiment. While not illustrated, such adjusting means can be obtained also, for example, by attaching thread- or ribbon-like elastic member to an elastically non-stretchable nonwoven fabric.

The chassis 1 further includes a plurality of thread-like elastic members 16 contractibly provided along side flaps 15 respectively defining the leg-openings 8. These elastic members 16 are secured in a stretched state within the respective side flaps 15 using hot melt adhesives (not shown) so that the side flaps 15 may be formed with gathers as these elastic members are relieved of the tension.

The chassis 1 additionally includes a pair of barrier cuffs 17 extending in parallel to each other in the longitudinal direction of the chassis 1 and formed from a liquid-resistant nonwoven fabric. These barrier cuffs 17 respectively have proximal side edge portions 17a joined to the upper surfaces of the respective side flaps 15 in the vicinity of side edges of the core 11 by means of hot melt adhesives or welding means (not shown). The barrier cuffs 17 respectively have distal portions 17b contiguous to the respective proximal side edge portions 17a and elasticized in the longitudinal direction of these distal portions 17b. Each of these distal portions 17b is elasticized by at least one thread-like elastic member 18 attached in a stretched state to the distal portion 17b along its upper side edge 17c.

Figure 4:
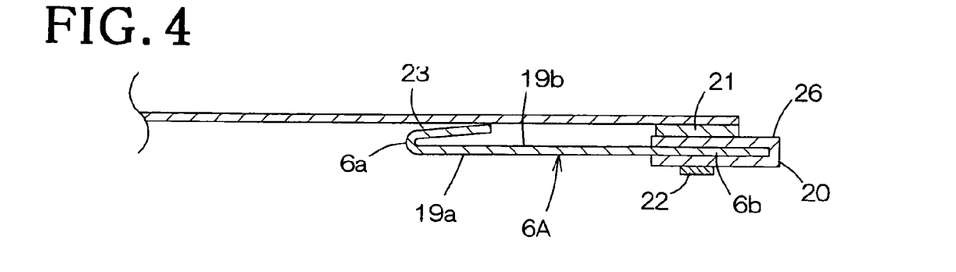
FIG. 4 is a sectional view taken along the line 4-4 in FIG. 1.

Referring to FIG. 4, each of the male fastener panels 6A has a body-facing surface 19a and a garment-facing surface 19b wherein at least the body-facing surface 19a is smooth. The male fastener panel 6A further has a distal end portion 6a and a proximal end portion 6b covered with a cover 20 made of a nonwoven fabric wherein these portions 6a, 6b are spaced from each other in the direction along the transverse axis of the chassis 1. The male fastener panel 6A is secured to the chassis 1 by means of a reinforcing member 21 made of a fibrous material such as a nonwoven fabric formed integrally with the side edge of the rear waist region 4 and a retainer piece 22 bonded to this reinforcing member 21. A coronoid hook 23 is formed on the distal end portion 6a and a finger-grip tab 26 is formed in contiguity to the proximal end portion 6b.

Preferably, the male fastener panel 6A is formed from plastics such as acrylic resin and has a stiffness value in a range of 0.09N/cm to 3N/cm as measured by the Taber's method. Preferably, the male fastener panel 6A has a dimension in a range of 5 to 50 mm as measured in the direction along the longitudinal axis of the chassis 1 and a dimension in a range of 20 to 60 mm as measured in the direction along the transverse axis of the chassis 1. Combination of such materials and dimensions appropriately selected to form the male fastener panel 6A with such dimensioning as indicated above allows the male fastener panel 6A to curve in conformity with a contour of the wearer's body and thereby to function as an effective stabilizing support means. This function is achieved without any deleterious effects such that the male fastener panel 6A might uncomfortably irritate the wearer's skin and/or might be distorted due to the movement of the wearer's body. It should be understood here that the male fastener panel 6A may be formed also from, instead of plastics, a cardboard having a surface resin finished to provide the cardboard with a desired stiffness.

Figure 5:
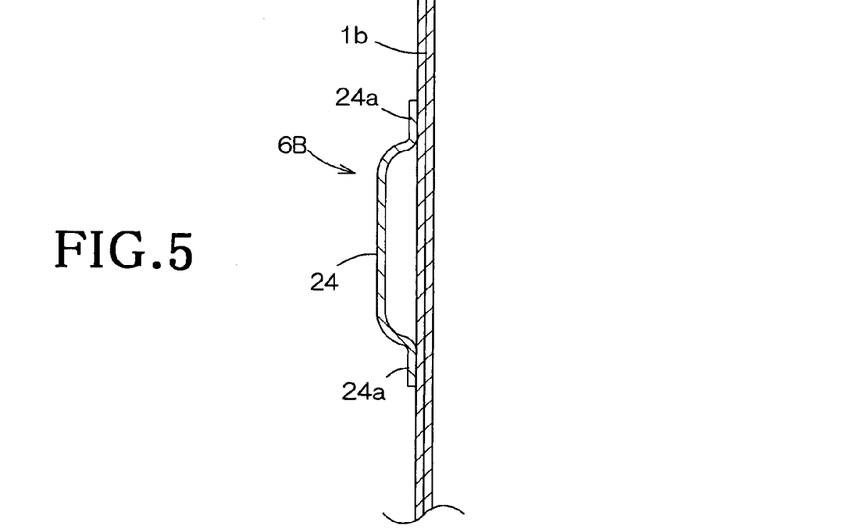
FIG. 5 is a sectional view taken along the line 5-5 in FIG. 1.

Referring to FIG. 5, the female fastener members 6B adapted to be engaged with the male fastener panels 6A are formed here by a string-like pieces 24 made of a fibrous material and defining loops on the outer surface 1b of the respective side edges of the front waist region 3. Each of these string-like pieces 24 has longitudinally opposite ends 24a and transversely opposite side edges 24b, 24c wherein the string-like piece 24 have the respective ends 24a secured to the outer surface 1b at predetermined positions thereon.

Figure 6:
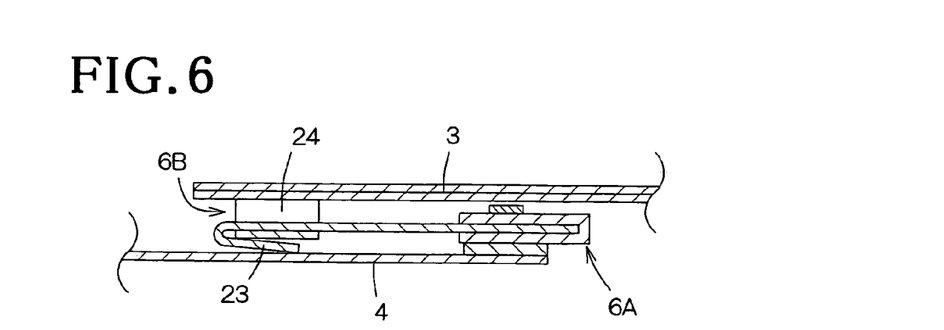
FIG. 6 is a sectional view taken along the line 6-6 in FIG. 1.
Figure 7:
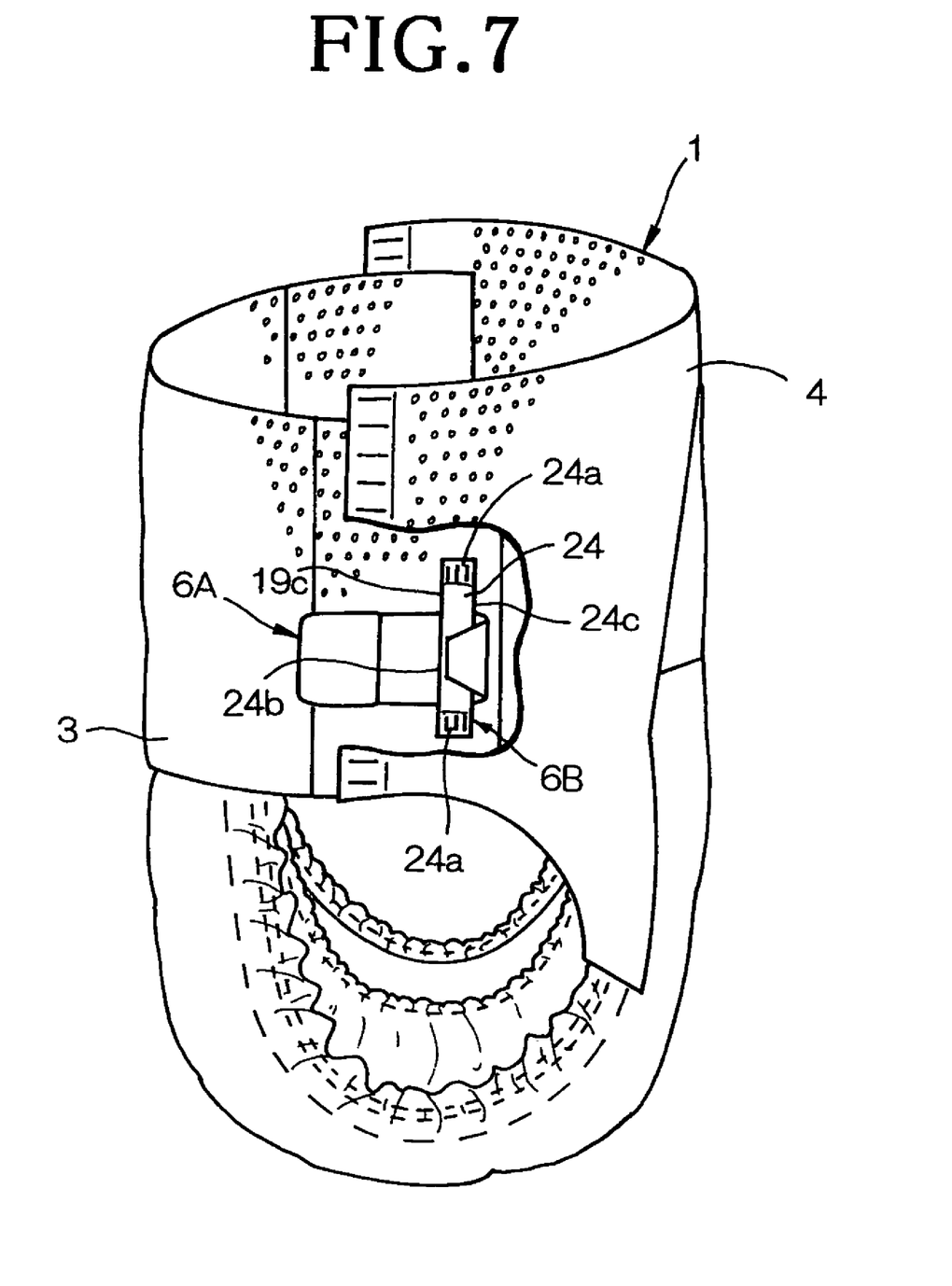
FIG. 7 is a side view showing the diaper in its assembled state.

As will be apparent from FIGS. 6 and 7, the article is assembled by inserting the male fastener member 6A into the string-like piece 24 first through the one side edge 24b and then through the other side edge 24c. Depending on a circumferential waist size of the particular wearer, the hook 23 engages the associated string-like piece 24 from the other side edge. While such operation of assembling is usually carried out with the article placed at appropriate position about the wearer's body, it is also possible to assemble the article before placed about the wearer's body. With the article put on the wearer's body, the front and rear waist regions 3, 4 are in a stretched and tensioned condition against an elastic contractility thereof and the side edges of the rear waist region 4 press the male fastener panels 6A. Under such a condition, the male fastener panels 6A are tightly held between the wearer's waist and the side edges of the rear waist region 4 facing away from the wearer's body with interposition of the side edges of the front waist region 3 facing the wearer's body. So far as the male fastener panels 6A are reliably held on predetermined positions in this manner, the hooks 23 are not essential elements. In such a situation, a considerably high shearing force is exerted on the side edges of the front and rear waist regions 3, 4 overlapping one another. The higher the shearing force, the more reliably the side edges of the front and rear waist regions are pressed against one another. In this way, the front and rear waist regions 3, 4 are reliably connected and position-stabilized by means of the male fastener members 6A.

Figure 8:
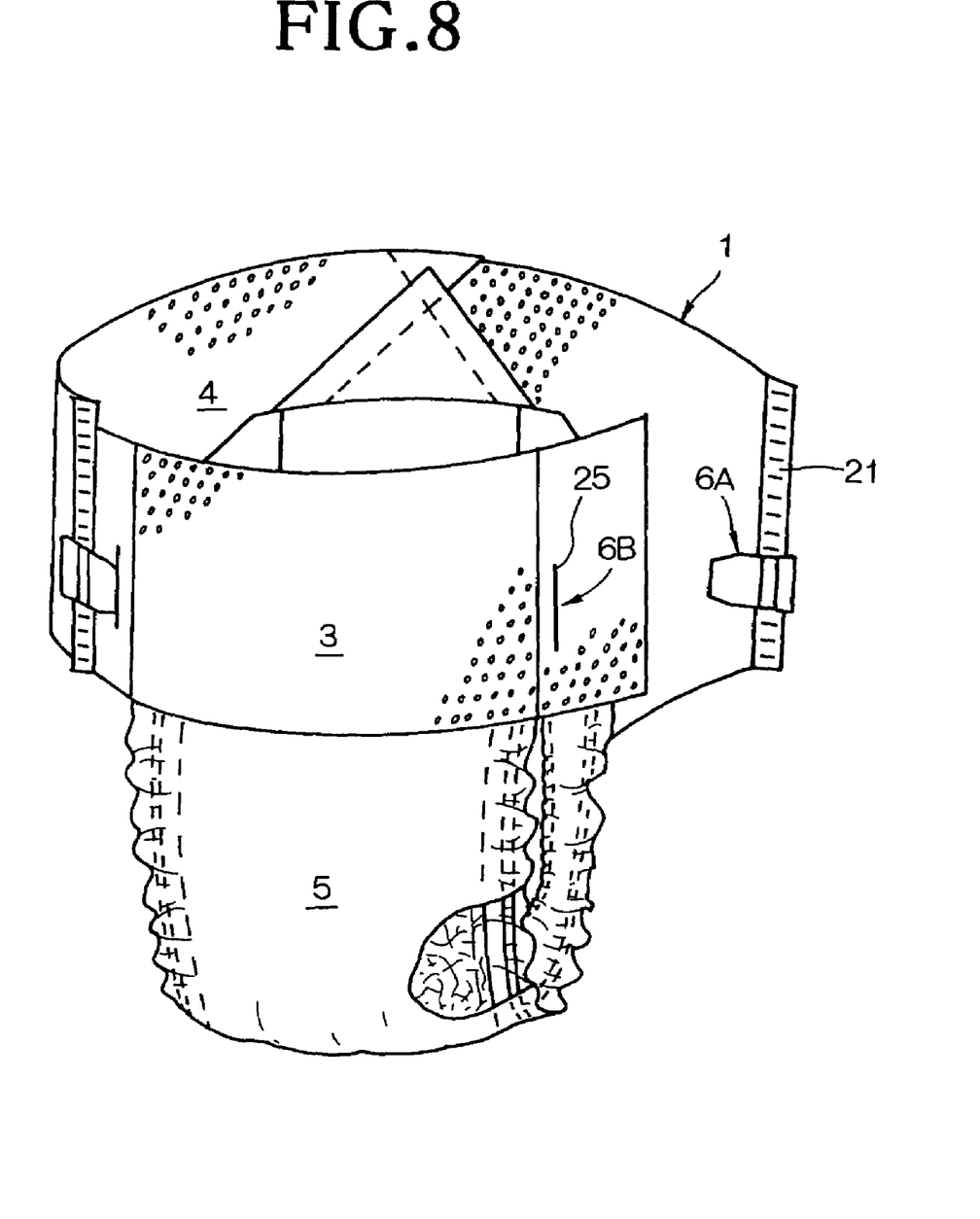
FIG. 8 is a view similar to FIG. 1, showing the diaper according to one preferred embodiment of the invention.
Figure 9:
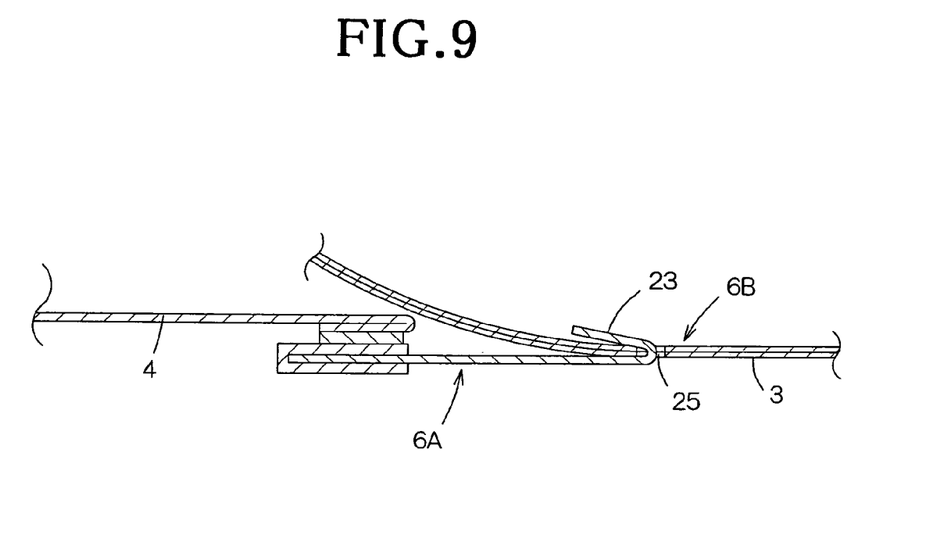
FIG. 9 is a sectional view similar to FIG. 6, showing the diaper according to the embodiment of FIG. 8.

FIGS. 8 and 9 show another embodiment of the present invention. According to this embodiment, the female fastener members 6B are defined by slits 25 formed at predetermined positions on the side edges of the front waist region 3. The male fastener panels 6A may be inserted into the respective slits 25 to connect the front and rear waist regions 3, 4 with each other. The other constructions as well as functions of the article are substantially similar to those in the previously described embodiment with reference to FIGS. 1 through 7. Therefore, the components similar to those constituting the embodiment of FIGS. 1 through 7 are designated by the similar reference numerals and description thereof will be eliminated.

Figure 10:
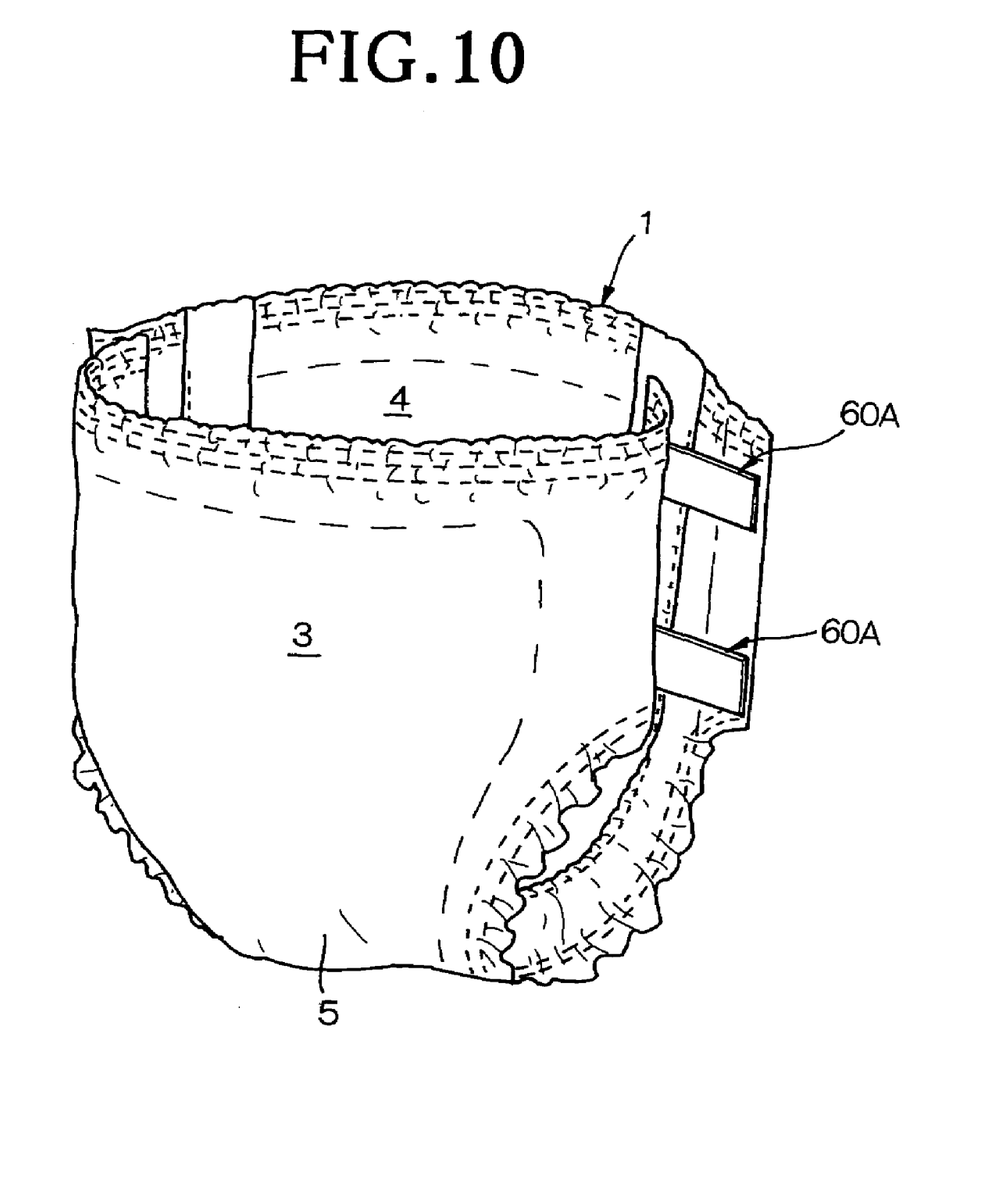
FIG. 10 is a perspective view showing a diaper according to another preferred embodiment.
Figure 11:
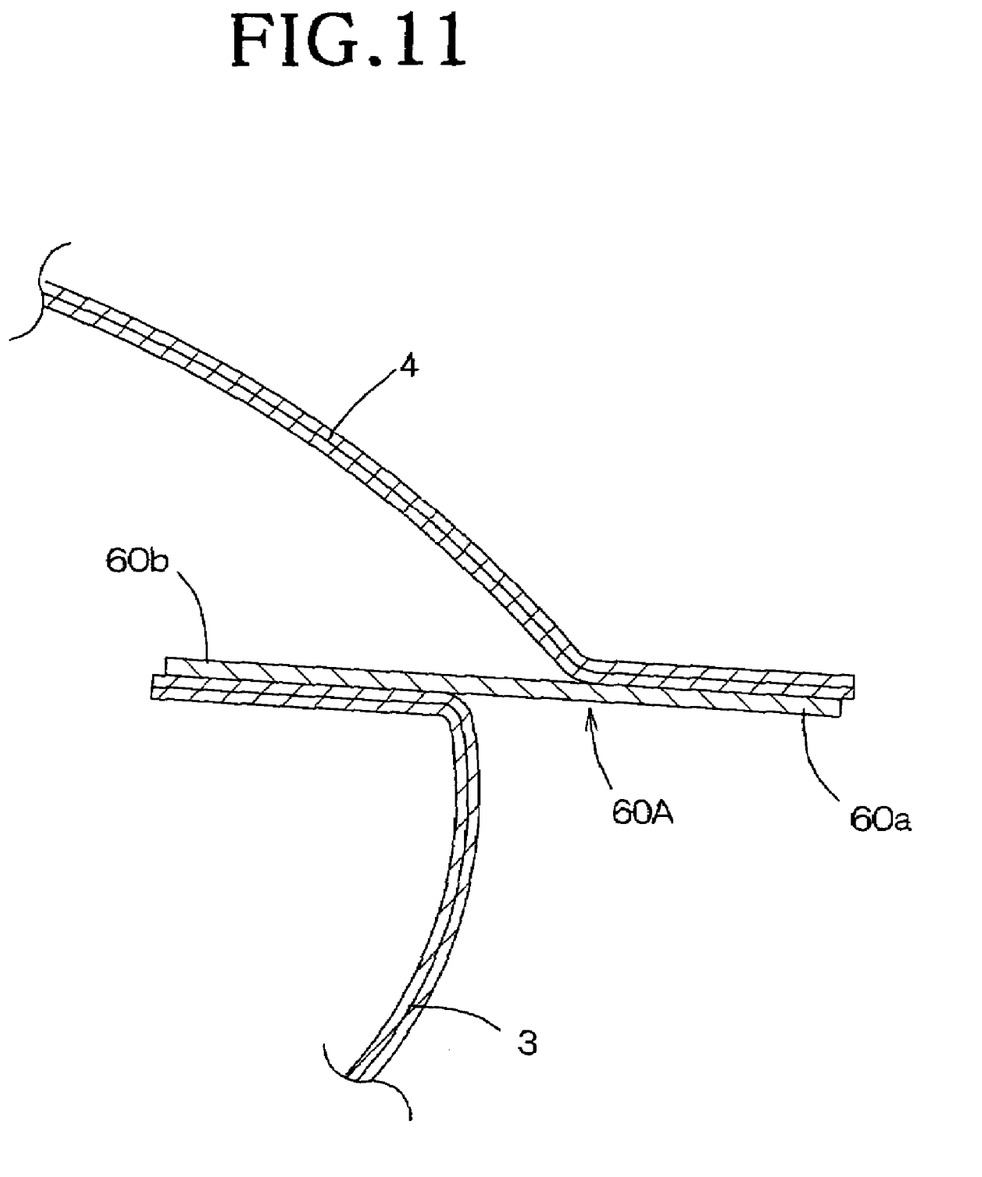
FIG. 11 is a sectional view showing a fastening mechanism adopted in the embodiment of FIG. 10.

FIGS. 10 and 11 show still another embodiment of the present invention. According to this embodiment, the article is provided on each of its side edges with a pair of fastener panels 60A. In contrast with the fastener panels 60A, these panels 60A have none of the hooks and require none of the female fastener members 6B with which these panels 60A should cooperate. Each of these fasteners 60A has a first end 60a secured to the inner surface of the side edge of the rear waist region 4 and a second end 60b is secured to the outer surface of the front waist region 3. The other constructions as well as functions of the article are substantially similar to those in the previously described embodiment with reference to FIGS. 1 through 7. Therefore, the components similar to those constituting the embodiment of FIGS. 1 through 7 are designated by the similar reference numerals and description thereof will be eliminated.

The inner and outer sheets 9, 10 as well as the core 11 may be formed from materials conventionally used for the disposable diaper of well known art. Specifically, materials for the inner sheet 9 includes, in addition to a fibrous nonwoven fabric, a porous plastic film, materials for the outer sheet 10 includes, in addition to a plastic film, a moisture-pervious plastic film and a laminate consisting of such moisture-pervious plastic film and a fibrous nonwoven fabric and materials for the core 11 includes a mixture of fluff pulp and super-absorbent polymer particles.

Materials for the elastic members 16, 18 may be also selected from those conventionally used for the disposable diaper of well known art such as a natural rubber, a synthetic rubber and a urethane foam.

The sheet members 12, 13 and the intermediate segment 14a of the belt-like member 14 may be formed from a stretch- and contractable nonwoven fabric of well known art. The end segments 14b of the belt-like member 14 also may be formed from an elastically non-stretchable nonwoven fabric of well known art.

What is claimed is:

1. A wearing article, comprising:
a chassis having a longitudinal direction, a transverse direction orthogonal to said longitudinal direction, an inner surface adapted to face a wearer in use, an outer surface adapted to face away from the wearer in use, first and second waist regions cooperating with each other in use to define a waist-opening, and a crotch region extending in the longitudinal direction between said first and second waist regions and cooperating with said two waist regions in use to define a pair of leg-openings;
a fastening system for releasably connecting said first and second waist regions with each other along transversely opposite side edges thereof;
an elastic adjusting element located in at least one of said first and second waist regions for stretching or contracting said at least one waist region in said transverse direction;
said fastening system comprising:
a pair of male fastener members each in the form of a panel having a stiffness value in a range of 0.09N/cm to 3N/cm as measured by the Taber's method and comprising, in the transverse direction, opposite distal and proximal ends, wherein said distal end has a V- or U-shaped hook and extends inward in the transverse direction from the respective proximal end toward a longitudinal axis of said article, and said proximal end is secured to a respective one of said transversely opposite side edges of said first waist region; and
a pair of female fastener members located on said transversely opposite side edges of said second waist region and releasably engageable with said male fastener members, respectively, wherein each of said female fastener members is defined by a loop positioned on the outer surface and elongated in the longitudinal direction along a respective one of the transversely opposite side edge of said second waist region;
wherein, in each of said male fastener members, the distal portion has
a first portion extending inwardly in the transverse direction from the proximal portion while being spaced from the inner surface of said first waist region, and
a terminal, second portion extending outwardly in the transverse direction from the first portion toward the proximal portion, and obliquely toward the inner surface of said first waist region to define, together with said first portion, the hook;
wherein said second portion is located, as seen in a thickness direction of the first waist region, between said first portion and the inner surface of said first waist region; and
wherein, when the hook of each of the male fastener members is engaged with the loop of the corresponding female fastener member, a section of the loop is located, as seen in the thickness direction of the first waist region, between said first and second portions of the distal portion of said male fastener member,
wherein each of said male fastener members has
the proximal end directly secured to the inner surface of said first waist region along the respective side edge of the first waist region, and
a finger-grip tab extending outward in said transverse direction from the proximal end, away from the distal end and beyond the respective side edge of the first waist region, wherein said proximal end is located, as seen in the transverse direction, between said distal end and said finger-grip tab.

2. A wearing article, comprising:
a chassis having a longitudinal direction, a transverse direction orthogonal to said longitudinal direction, an inner surface adapted to face a wearer in use, an outer surface adapted to face away from the wearer in use, first and second waist regions cooperating with each other in use to define a waist-opening, and a crotch region extending in the longitudinal direction between said first and second waist regions and cooperating with said two waist regions in use to define a pair of leg-openings;
a fastening system for releasably connecting said first and second waist regions with each other along transversely opposite side edges thereof;
an elastic adjusting element located in at least one of said first and second waist regions for stretching or contracting said at least one waist region in said transverse direction;
said fastening system comprising:
a pair of male fastener members each in the form of a panel having a stiffness value in a range of 0.09N/cm to 3N/cm as measured by the Taber's method and comprising, in the transverse direction, opposite distal and proximal ends, wherein said distal end has a V- or U-shaped hook and extends inward in the transverse direction from the respective proximal end toward a longitudinal axis of said article, and said proximal end is secured to a respective one of said transversely opposite side edges of said first waist region; and
a pair of female fastener members located on said transversely opposite side edges of said second waist region and releasably engageable with said male fastener members, respectively, wherein each of said female fastener members is defined by one of (i) a loop positioned on the outer surface and elongated in the longitudinal direction along a respective one of the transversely opposite side edge of said second waist region, and (ii) a slit provided in said second waist region and elongated in the longitudinal direction along the respective one of the transversely opposite side edge of said second waist region;
wherein, in each of said male fastener members,
the proximal portion is directly attached to the inner surface of said first waist region; and
the distal portion has a first portion substantially parallel with and spaced from the inner surface of said first waist region, and further has a terminal, second portion extending in the transverse direction outwardly toward the proximal portion and obliquely toward the inner surface of said first waist region and defining said hook;
wherein said second portion is located, as seen in a thickness direction of the first waist region, between said first portion and the inner surface of said first waist region; and
wherein, when the hook of each of the male fastener members is engaged with the loop or slit of the corresponding female fastener member, a section of the loop or a section of the second waist region defining the slit is located, as seen in the thickness direction of the first waist region, between said first and second portions of the distal portion of said male fastener member, wherein each of said male fastener members further comprises a finger-grip tab extending outward in said transverse direction from said proximal end, away from the distal end and beyond the respective one of said transversely opposite side edges of the first waist region, wherein said proximal end is located, as seen in the transverse direction, between said distal end and said finger-grip tab.

3. A wearing article, comprising:

a chassis having a longitudinal direction, a transverse direction orthogonal to said longitudinal direction, an inner surface adapted to face a wearer in use, an outer surface adapted to face away from the wearer in use, first and second waist regions cooperating with each other in use to define a waist-opening, and a crotch region extending in the longitudinal direction between said first and second waist regions and cooperating with said two waist regions in use to define a pair of leg-openings; and a fastening system for releasably connecting said first and second waist regions with each other along transversely opposite side portions thereof;

said fastening system comprising:

a pair of male fastener members each in the form of a panel having, in the transverse direction, opposite distal and proximal ends, wherein said distal end extends inward in the transverse direction from the respective proximal end and defines a hook, and said proximal end is secured to a respective one of said transversely opposite side portions of said first waist region; and a pair of female fastener members located on the outer surface of said transversely opposite side portions of said second waist region and releasably engageable with said male fastener members, respectively, wherein each of said female fastener members is defined by a loop;

wherein, when the hook of each of the male fastener members is releasably engaged with the loop of the corresponding female fastener member, the respective side portion of the first waist region overlaps the corresponding side portion of the second waist regions, and both said hook and loop are entirely located, as seen in a thickness direction of the first and second waist regions, between the overlapping side portions of said first and second waist regions, wherein, in each of said male fastener members, the proximal portion is directly attached to the inner surface of said first waist region; and the distal portion has a first portion extending inwardly in the transverse direction from the proximal portion while being spaced from the inner surface of said first waist region, a terminal, second portion extending in the transverse direction outwardly from an innermost end of the first portion toward the proximal portion and defining, together with said first portion, the hook; and a finger-grip tab extending outward in said transverse direction from said proximal end, away from the distal end and beyond a longitudinal edge of the respective one of said transversely opposite side portions of the first waist region;

wherein said second portion is located, as seen in the thickness direction of the first waist region, between said first portion and the inner surface of said first waist region; and wherein said proximal end is located, as seen in the transverse direction, between said distal end and said finger-grip tab.

4. The article as defined by claim 3, wherein, when each said loop is releasably engaged with the respective hook, a portion of the loop is received, as seen in said thickness direction of the waist regions, between the first and second portions of the distal portion of said male fastener member.

5. The article as defined by claim 4, wherein the distal end of each said male fastener member consists of only one said hook.

6. The article as defined by claim 5, wherein each said female fastener member consists of only one said loop.

7. The article as defined by claim 4, wherein, when the hook of each of the male fastener members is releasably engaged with the loop of the corresponding female fastener member, the second portion is located, as seen in the thickness direction of the first and second waist regions, between said portion of the loop and the inner surface of the respective side portion of the first waist region, and the first portion is located, as seen in the thickness direction of the first and second waist regions, between said portion of the loop and the outer surface of the respective side portion of the second waist region.

8. The article as defined by claim 4, wherein, when the hook of each of the male fastener members is releasably engaged with the loop of the corresponding female fastener member, the only part of said male fastener member that is not sandwiched between the overlapping side portions of said first and second waist regions is the finger-grip which is exposed on the outer surface of the second waist region for handling by a user.

* * * * *